(12) United States Patent
Smink et al.

(10) Patent No.: US 10,638,977 B2
(45) Date of Patent: May 5, 2020

(54) ELECTRO-CARDIOGRAPH SENSOR MAT

(71) Applicant: Koninklijke Philips N.V., Eindhoven (NL)

(72) Inventors: Jouke Smink, Eindhoven (NL); Steffen Weiss, Eindhoven (NL); Sascha Krueger, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 370 days.

(21) Appl. No.: 15/641,388

(22) Filed: Jul. 5, 2017

(65) Prior Publication Data
US 2018/0125428 A1 May 10, 2018

Related U.S. Application Data

(63) Continuation of application No. 14/370,990, filed as application No. PCT/IB2013/050021 on Jan. 2, 2013, now Pat. No. 9,706,961.

(60) Provisional application No. 61/584,870, filed on Jan. 10, 2012.

(30) Foreign Application Priority Data

Jan. 10, 2012 (EP) ..................................... 12150541

(51) Int. Cl.
*A61B 5/0408* (2006.01)
*A61B 5/00* (2006.01)
*A61B 5/0428* (2006.01)
*A61B 5/055* (2006.01)

(52) U.S. Cl.
CPC ........ *A61B 5/6892* (2013.01); *A61B 5/04085* (2013.01); *A61B 5/04288* (2013.01); *A61B 5/6804* (2013.01); *A61B 5/6805* (2013.01); *A61B 5/055* (2013.01)

(58) Field of Classification Search
CPC ............ A61B 5/04085; A61B 5/04288; A61B 5/6804; A61B 5/6805; A61B 5/6892; A61B 5/7203
See application file for complete search history.

(56) References Cited

U.S. PATENT DOCUMENTS

| 5,782,238 A | 7/1998 | Beitler |
| 6,032,063 A | 2/2000 | Hoar |
| 6,052,614 A | 4/2000 | Morris |

(Continued)

FOREIGN PATENT DOCUMENTS

JP 04071536 A 4/2008

OTHER PUBLICATIONS

Mullinger et al "Effects of Simultaneous EEG Recording on MRI Data Quality at 1.5, 3 and 7 Tesla" International Journal of Psychophysiology 67 (2008) p. 178-188.

(Continued)

*Primary Examiner* — Lee S Cohen

(57) ABSTRACT

The invention relates to an electrocardiograph sensor mat (100), the mat (100) comprising a multitude of electrodes (104) for acquiring cardiac signals and a plug (200), wherein the electrodes (104) are connected to the plug (200) by electric wires (102), wherein the wires (102) are segmented by switches (202), wherein the switches (202) are switchable between a closed state and an open state, wherein in the closed state the electrodes (104) are electrically connected to the plug (200) and wherein in the open state the electrodes (104) are electrically isolated from the plug (200).

20 Claims, 3 Drawing Sheets

(56) References Cited

U.S. PATENT DOCUMENTS

2006/0247509 A1    11/2006   Tuccillo
2009/0256574 A1    10/2009   Weiss
2010/0244826 A1     9/2010   Schmidig
2011/0028822 A1     2/2011   Beck

OTHER PUBLICATIONS

Weiss et al "In Vivo Evaluation and Proof of Radiofrequency Safety of a Novel Diagnostic-MR-Electrophysiology Catheter" Magnetic Resonance in Med. 65, p. 770-777 (2011).

Weiss et al "Evaluation of a Novel MR-RF Ablation Catheter With Full Clinical Functionality" Proc. Intl. Soc. Mag. Reson. Med 19 (2011) p. 2011.

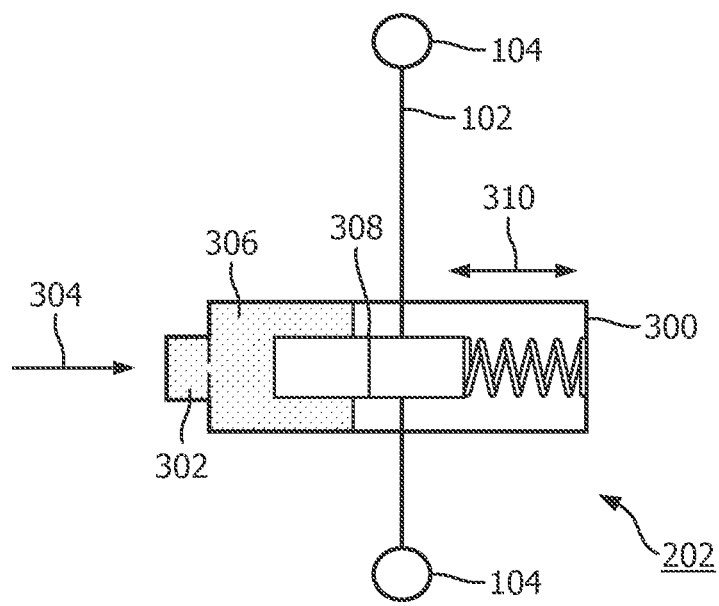
FIG. 3
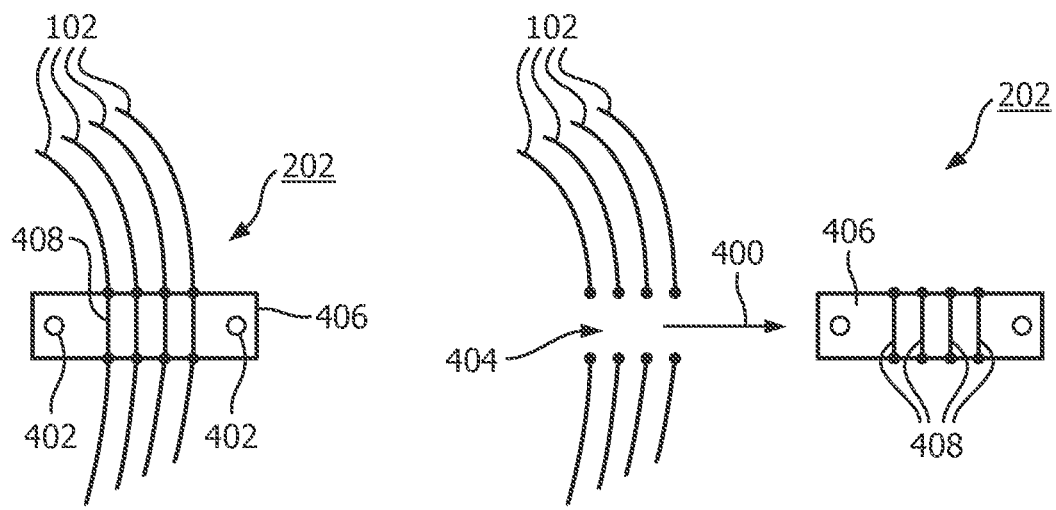
FIG. 4A
FIG. 4B

ELECTRO-CARDIOGRAPH SENSOR MAT

CROSS-REFERENCE TO PRIOR APPLICATIONS

This application a continuation of application Ser. No. 14/370,990, now U.S. Pat. No. 9,706,961, which is the U.S. National Phase application under 35 U.S.C. § 371 of International Application No. PCT/IB2013/050021, filed on Jan. 2, 2013, which claims the benefit of U.S. Provisional Patent Application No. 61/584,870, filed on Jan. 10, 2012 and European Patent Application No. 12150541.6, filed on Jan. 10, 2012. These applications are hereby incorporated by reference herein.

FIELD OF THE INVENTION

The invention relates to an electrode cardiograph sensor mat.

BACKGROUND OF THE INVENTION

Heart disease is the number one cause of death in the world. Abnormal electric activity of the heart due to for example cardiac arrhythmia, including atrial fibrillation (AF) and ventricular tachycardia (VT) and congestive heart failure (CHF) are the fastest growing areas for both clinical and industrial development.

Electro-cardiographic mapping (ECM) is a non-invasive technique that provides detailed cardiac electrical activity information for the entire heart for each heartbeat by combining body surface electrical data acquired from a large number of surface electrodes with detailed three-dimensional anatomical data obtained from for example computer tomography (CT). It thus has the potential to deliver detailed electrophysiological information, which otherwise can only be measured with cardiac catheters in invasive electrophysiologic procedures. Additionally, ECM provides truly time-resolved transient electrophysiological data and multi-chamber information, while catheter data can only be acquired locally as a function of the cardiac cycle. Improved mapping and localization technologies as ECM will be critical to ongoing efforts to better diagnose and treat the above mentioned disease states.

FIG. 1 illustrates an image of a state of the art prototype ECM vest. The ECM vest is a multi-electrode vest (designated by reference numeral 100) with two multi-connector plugs for simple and fast connection of all individual electrodes 104. The individual electrodes 104 are connected to the multi-connector plugs via electric wires 102.

While FIG. 1a depicts a photographic image of the ECM vest, FIG. 1b depicts an X-ray image of the vest showing enlarged the arrangement of the electric wires 102 in more detail. As can be clearly seen, the close-up view in FIG. 1b shows that a multitude of electric wires are bundled in order to interconnect the electrodes 104 with the above mentioned multi-connector plug. Typically, each electrode is assigned a dedicated wire.

Multi-electrode vests for ECM like the one depicted in FIG. 1 will become important, both, as non-invasive diagnostic tools and during electrophysiological interventions where they can be used concurrently with catheters to obtain intracardiac signals. This avoids and shortens lengthy point-to-point mapping procedures or the necessity of large multi-electrode mapping devices.

Further, the U.S. Pat. No. 5,782,238 discloses an EKG devices comprising a pad with multiple electrodes. The electrodes are grouped into sets of electrodes, each correspond to a particular body size.

However, ECM requires the knowledge of the exact location of the surface electrodes in relation to the patient anatomy, including the cardiac anatomy. Herein, a 'patient' may be either a human being or an animal. For diagnostic use, the exact location of the electrodes in relation to the patient anatomy is currently obtained by computer tomography (CT).

SUMMARY OF THE INVENTION

It is an object of the invention to provide for an improved electro-cardiograph sensor mat. This problem is solved by the independent claims. Preferred embodiments are described in the dependent claims.

In accordance with the invention, an electro-cardiograph sensor mat is provided, wherein the mat comprises a multitude of electrodes for acquiring cardiac signals and a plug, wherein the electrodes are connected to the plug by electric wires, wherein the wires are segmented by switches, wherein the switches are switchable between a closed state and an open state, wherein in the closed state the electrodes are electrically connected to the plug and wherein in the open state the electrodes are electrically isolated from the plug.

Embodiments of the invention may have the advantage that the exact location of the electrodes of the sensor mat in relation to the patient anatomy can be obtained by magnetic resonance imaging (MRI). MRI has the advantage that it is very sensitive to soft tissue contrast and thus permits to determine in a highly exact manner the patient anatomy. Further, the advantage of MRI is that radiation occurring in CT is avoided. Further, during interventions performed for example in a combined X-ray and magnetic resonance (MR) interventional suite (XMR) or even MRI only setup, magnetic resonance imaging may be additionally used to visualize ablated structures and then ablation and mapping may be continued, again using the vest. Ablation can be performed for example using patient-specific cardiac radio-frequency ablation.

Embodiments of the present invention may be advantageous since for example the electro-cardiograph sensor mat may be changed between an MR non-compatible and an MR compatible state in an easy and fast manner. The kind of ECG vests, for example as the one depicted in FIGS. 1A and 1B, cannot be used safely in MRI, since the long conducting leads 102 are directly adjacent to the skin (with high dielectric constant). The leads 102 may be subject to resonances around the resonant frequency of the MR scanner. This leads to potential heating at the ends of the wires, which means in particular at the electrodes. However, since the electrodes need to be directly adjacent to the skin, there is a high risk of skin burning due to the heating.

Further, RF coupling of the tightly packed leads as seen in FIG. 1B may lead to multiple resonances, which are hard to predict or model. Additionally, the presence of the leads 102 leads to $B_1$ artifacts in the MR images.

Embodiments of the present invention may solve all these problems by providing a switchable segmentation of the wires, such that local currents induced by a magnetic resonance imaging process are minimized in the leads. This also minimizes heating of the ends of the leads and the occurrence of artifacts in MR images due to the presence of the leads in the mat.

It has to be noted here, that embodiments of the present invention may also have the advantage that the usage of RF traps or similar devices inside the vest is avoided. Typical RF traps are bulky, may heat up themselves and it is rather difficult to predict how RF traps couple with a heavily wired environment.

Generally, image-forming MR methods, which utilize the interaction between magnetic field and nuclear spins in order to form two-dimensional or three-dimensional images are widely used nowadays, notably in the field of medical diagnostics, because for the imaging of soft tissue they are superior to other imaging methods in many respects, they do not require ionizing radiation, and they are usually not invasive. MRI is used for example as imaging technique to visualize myocardial injury. Cardiac and respiratory triggered MR imaging can be used to image morphology, time resolved cine movies may reveal cardiac function, dynamic contrast enhanced imaging can be utilized to measure perfusion and MR tagging sequences can be used to study the contraction of the myocardium in detail.

According to the MR method in general, the body of a patient or in general an object to be examined is arranged in a strong, uniform magnetic field $B_0$ whose direction at the same time defines an axis, normally the z-axis, of the coordinate system on which the measurement is based.

The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a precessional motion about the z-axis.

Any variation of the magnetization can be detected by means of receiving RF antennas, which are arranged and oriented within an examination volume of the MR device in such a manner that the variation of the magnetization is measured in the direction perpendicularly to the z-axis.

In order to realize spatial resolution in the body, switching magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body.

The signal data obtained via the receiving antennas corresponds to the spatial frequency domain and is called k-space data. The k-space data usually includes multiple lines acquired with different phase encoding. Each line is digitized by collecting a number of samples. A set of samples of k-space data is converted to an MR image, e.g. by means of Fourier transformation.

In accordance with an embodiment of the invention, the switches are mechanical switches. For example, the switches are operable by pressurized gas, wherein the mat comprises an interface for receiving a connector supplying the gas and for providing a gas connection with the switches. This may have the advantage that an MR safe possibility of operating the switches can be provided. No further electrical connections for operating of the switches are required, which may further disturb the MR image acquisition process.

In accordance with an embodiment of the invention, the switches are adapted for being switched from the open state to the closed state upon reception of the gas in a pressurized state. This may have the advantage that MR safety in the passive, i.e. in the non-pressurized state, can be ensured.

In accordance with a further embodiment of the invention, the switches are adapted for automatically switching from the closed state to the open state upon a release of the pressurized gas. Again, this also may have the advantage that MR safety of the mat is ensured. Further, this may permit to reuse the electro-cardiograph sensor mat a multitude of times due to the reversibility of the switching process.

In accordance with a further embodiment of the invention, the mechanical switches comprises removable conducting elements, wherein the elements are fixed to a removable layer, wherein the switches are adapted for being switched from the closed state to the open state upon movement of the layer. In this alternative embodiment MR safety can be ensured by simply removing the layer comprising the removable conducting elements. Preferably, such a layer should be marked in a clearly visual manner such that an operator of the MR apparatus is easily able to check if the mat is in its MR safety state or not. Preferably, the vest and the layer should be marked for example by colors in such a manner that the MR safe state and the MR non-safe state are easily distinguishable.

In accordance with an embodiment of the invention, the movement comprises a removal of the layer from the mat. However, it is also possible that the movement of the layer is just a movement in form of a shifting of the layer in a predefined direction of the sensor mat. In this case, the shifting of the layer in the predefined direction may switch the switches between the open and the closed state.

In accordance with a further embodiment of the invention, the layer is fixable to the mat by fastening means. This has the advantage that during the electro-cardiographic measurements a movement of the patient will not lead to an unintended operation of the switches by an unintended movement of the removable layer. The fastening means thus precisely define the position of the removable layer with respect to the sensor mat.

In accordance with an embodiment of the invention, the fastening means for example comprise patent fasteners.

In accordance with a further embodiment of the invention, the segmentation by the switches results in segments, wherein the length of the segments is equal or less than an optimal length, wherein the optimal length is given by a length at which a magnetic resonance scan of an object carrying the mat results in a magnetic resonance image with artifacts due to the presence of the wires being below a predefined threshold and/or in a local heating of the electrodes and the segments due to magnetic resonance scan-induced Eddy-currents being below a predefined threshold. Notably, the length(s) of segments of the electric wires is (are) less than ¼ of the Larmor wavelength (corresponding to the Larmor frequency) associated with the magnetic field strength of the magnetic resonance examination system and with the gyromagnetic ratio of the type of nucleus at issue (usually protons ($^1$H)). This segmentation in than less than ¼λ segments suppresses RF resonances in the electric wires. Further, the width of the wires is made small so that Eddy currents (e.g. due to switching of the magnetic gradient of the magnetic resonance examination system) are not supported. Alternatively, the wires may be slitted longitudinally to suppress Eddy currents.

In accordance with a further embodiment of the invention, the mat is comprised in a garment, the garment being wearable by an object for performing the acquisition of the cardiac signals. For example, the garment is a vest. This permits to easily mount the electrodes to the object to be imaged.

In accordance with a further embodiment of the invention, the electric wires are not necessarily segmented but have a resistivity of at least 2 kOhm/m, preferably 5 kOhm/m. This has the advantage that potentially present RF resonances are further damped and thus MR image artifacts are further minimized. Nevertheless, this still allows the transmission of the ECG signal. Additionally segmenting the highly resistive wires may be used to further increase safety and/or reduce image artifacts.

In another aspect, the invention relates to an electro-cardiograph sensor mat, the mat comprising a multitude of electrodes for acquiring cardiac signals and a plug, wherein the electrodes are connected to the plug by electric wires, wherein the electric wires have a resistivity of at least 2 k Ohm/m, preferably 5 kOhm/m.

BRIEF DESCRIPTION OF THE DRAWINGS

The enclosed drawings with FIGS. 2, 3, 4A, and 4B disclose preferred embodiments of the invention. It should be understood, however, that the drawings are designed for the purpose of illustration only and not as a definition of the limits of the invention. In the drawings:

FIG. 3 illustrates a schematic of a switch, FIGS. 4A and 4B illustrate_a further schematic of a switch.

DETAILED DESCRIPTION

Figure 1A:
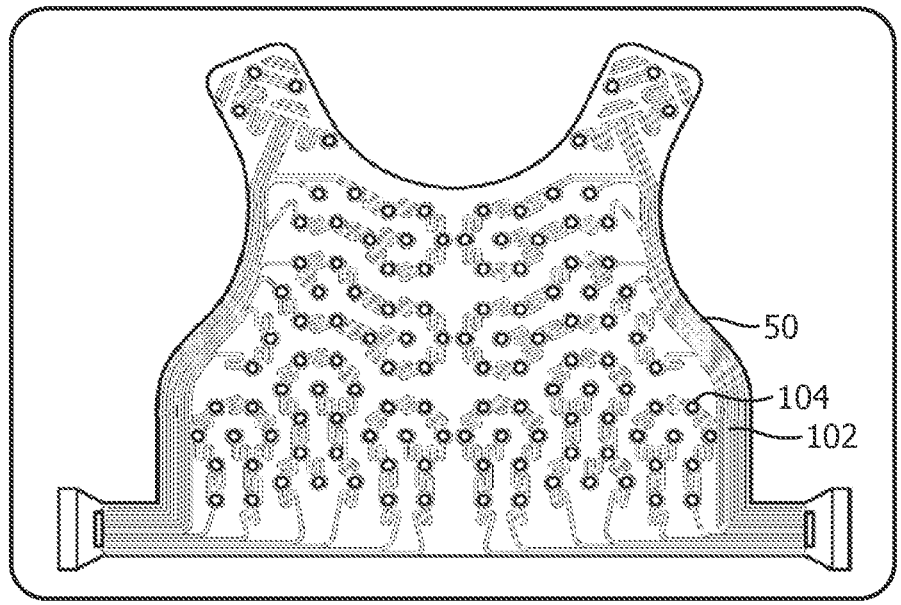
FIGS. 1A and 1B illustrate_an image of a state of the art prototype ECM vest.
Figure 1B:
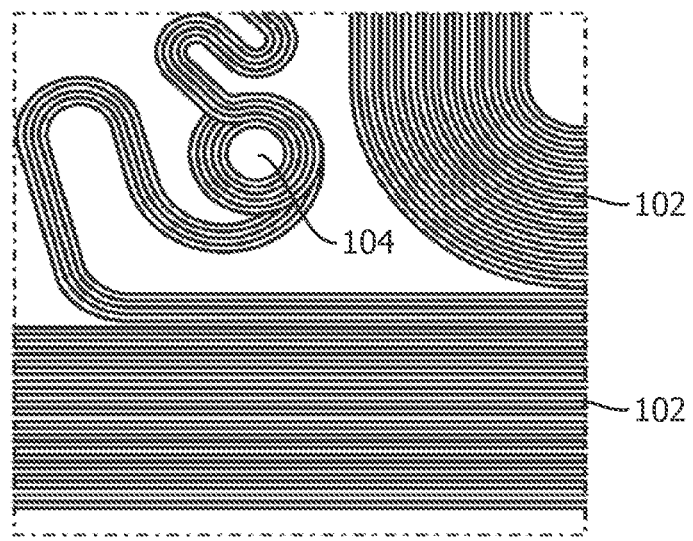

In the following, similar elements are depicted by the same reference numerals.

Figure 2:
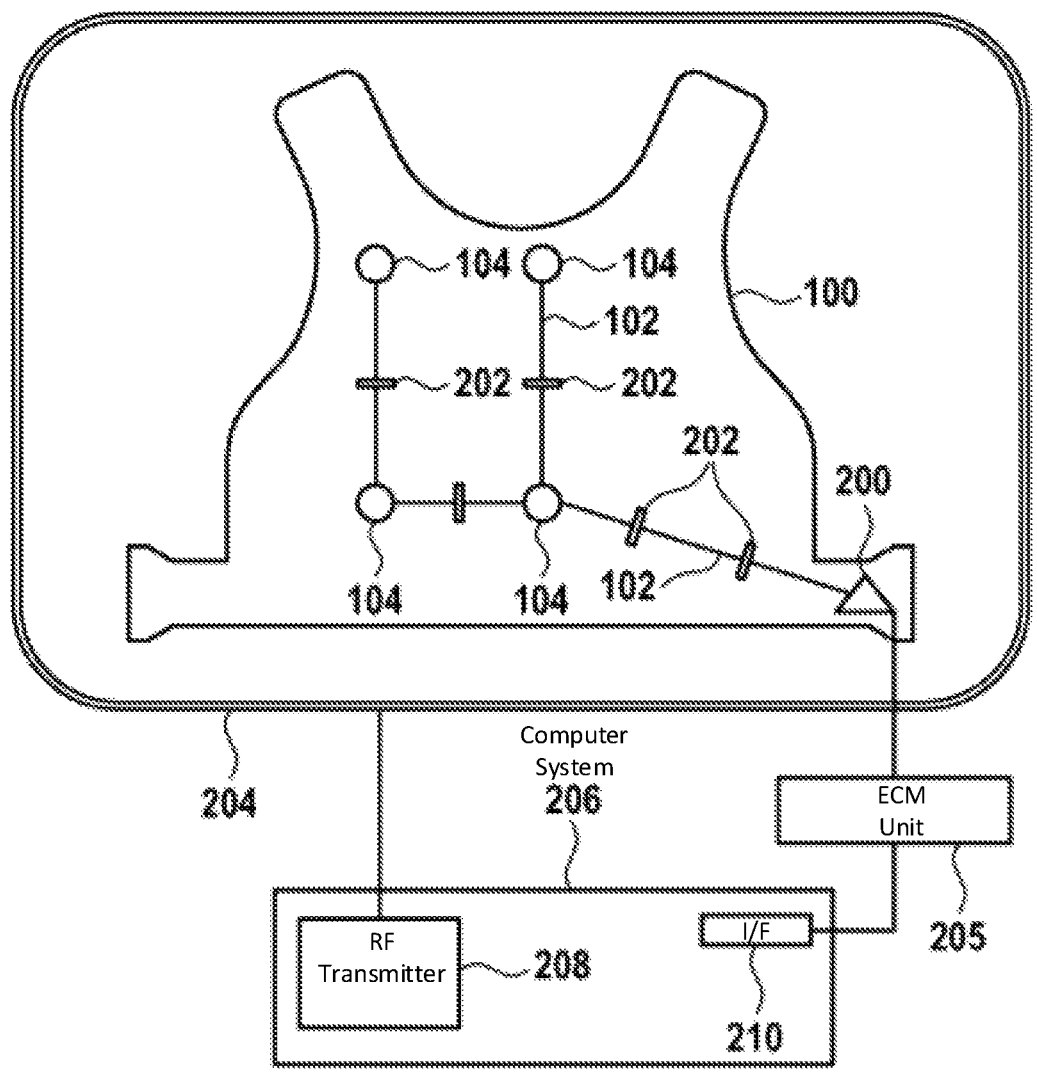
FIG. 2 illustrates a schematic of an electro-cardiograph sensor mat coupled to an MR imaging system.

FIG. 2 shows a schematic of an electro-cardiograph sensor mat 100. The mat comprises a multitude of electrodes 104 for acquiring cardiac signals of a patient. Preferably, the sensor mat is attached to the patient, for example worn by the patient. In this case, preferably the sensor mat is a vest worn by the patient.

The individual electrodes 104 are connected to a plug 200 of the vest 100. The connection is depicted by electric wires 102. The electric wires 102 are segmented by switches 202, wherein the switches are switchable between a closed state and an open state, wherein in the closed state the electrodes are electrically connected to the plug and wherein in the open state the electrodes are electrically isolated from the plug.

Further shown in FIG. 2 is an RF antenna 204 of a magnetic resonance imaging system. Typically, such a system comprises super-conducting or resistive main magnetic coils such that a substantially uniform, temporarily constant main magnetic field $B_0$ is created along a z-axis through an examination volume. Both, the vest 100 and the RF antenna 204 are located within the examination volume.

Typically, the magnetic resonance system applies a series of RF pulses in switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier applies current pulses to selected ones of whole body gradient coils along x, y and z-axis of the examination volume. An RF transmitter 208 transmits RF pulses or pulse packets via a send/receive switch to the RF antenna 204 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite, invert, refocus, or manipulate the magnetization of a portion of or the whole subject positioned in the examination volume. The resulting MR signals may also be picked up by the RF antenna 204.

As mentioned above, this magnetic resonance imaging process using the RF pulses is not only limited to the body positioned in the examination volume but also includes the vest 100. ECM requires the exact location of the electrodes of the electro-cardiograph sensor mat in relation to patient anatomy, such that it is important to also determine the exact position of the electrodes 104. Preferably, the electrodes may comprise a material which provides a strong MR signal. This permits to easily locate the exact location of the electrodes. For example, the electrodes may carry gel pads doped with an MR contrast agent to enhance signals which simplifies the determination of the electrode positions from the MR images.

For generation of MR images of limited regions of the patient and the vest 100, for example for parallel imaging, a set of local array RF coils are placed contiguous to the region selected for imaging. The array coils can be used to receive MR signals induced by RF transmissions effected via the RF antenna. However, it is also possible to use the array coils to transmit RF signals to the examination volume.

The resultant MR signals are picked up by the RF antenna 204 and/or by the array of RF coils and are then demodulated by a receiver preferably including a pre-amplifier. The receiver is connected to the RF coils via a send/receive switch.

A host computer controls the gradient pulse amplifier and the transmitter to generate any of a plurality of imaging sequences, such as echo-planar imaging (EPI), echo-volume imaging, gradient and spin-echo imaging, far spin-echo imaging, imaging using ultra-short echo time acquisition pulse sequences and the like.

For the selected sequence, the receiver receives a similar plurality of MR data lines in rapid succession following each RF excitation pulse. A data acquisition system performs analogue-to-digital conversion of the received signals and converts each MR data line to a digital format suitable for further processing. In modern MR systems the data acquisition system is a separate computer which is specialized in acquisition of raw image data.

Ultimately, the digital raw image data is reconstructed into an image representation by a reconstruction processor which applies a Fourier transform or other appropriate reconstruction algorithm. The MR image may represent a planar slice through the patient, an array of parallel planar slices, three-dimensional volume, arbitrarily shaped signal volumes, planes, pencils etc. or any other type of more or less complex spatial signal arrangements. The image is then stored in an image memory where it may be accessed for converting slices or other portions of the image representation into appropriate formats for visualization, for example via a video monitor which provides a man-readable display of the resultant MR image.

The system 206 depicted in FIG. 2 may for example be a dedicated computer system which performs the above-mentioned function of the host computer.

The plug 200 is connected to an ECM unit 205 by appropriate transmission means, either cables, optical transmission means or RF transmission means. Thus, the ECM unit 205 is able to receive the cardiac signals from the electrodes 104. The ECM unit 205 is designed to amplify, filter, process, store, and display the electro-cardiographic signals acquired with the ECM vest 100 for electro-cardiographic mapping purposes. This ECM unit 205 may also be equipped to operate the switches 202 of the ECM vest 100. The ECM unit 205 is further connected to the computer system 206 by an interface 210 of the computer system 206. Thus, the computer system 206 and the ECM unit 205 are able to communicate. Communication may be performed for the purpose of timing and coordinating of MR measurements and electro-cardiographic mapping.

FIG. 3 illustrates a switch 202 interposed between the electric wires 102 of two electrodes 104. The switch 202 is operable by pressurized gas. For this purpose, the switch 202 comprises a connector 302 through which gas can be provided into a chamber 306 of the switch. The supply of pressurized gas is indicated by the reference numeral 304. An interrupt contact 308 is movable in direction 310 between an open and a closed state of the switch 202. The interrupt contact is spring-operated using a spring 300. Upon reception of gas in a pressurized state through the connector 302, the chamber 306 is filled with gas. This results in an exertion of a pressure force onto the interrupt contact 308, which moves the contact from an open state depicted in FIG. 3 to a closed state. In the closed state, an electrical interconnection is given.

It has to be noted here that even though in FIG. 3 only a single wire 102 is shown which can interconnect the two electrodes, this does not necessarily mean that the electrodes need to be interconnected with each other. FIG. 3 is shown for illustrative purposes only and preferably, each electrode is connected individually to the plug mentioned above. Thus, an interconnection of the electrodes themselves is not necessary. Thus, in reality the interrupt contact comprises a multitude of individual contacts which are able to interconnect a multitude of electric wires 102.

Preferably, the air pressure operated switches 202 are distributed in the vest 100 along the wires. These switches are preferably addressed by thin plastic tubes contained in the vest. All plastic tubes concur at a central connection socket or connector where a pressure actuator can be attached. In the simplest case such a pressure actuator may be a syringe. Pumping air into this connector may close all switches for ECM operation. Release of the pressure opens the switches for MR scanning. This variant ensures MR safety in the passive, i.e. non-pressurized state. The embodiment further permits to switch the vest inside the MR coil even for a lying patient. This avoids relocation of the electrodes between ECG recording and MR scanning.

For example, the pumping of air into the connector and the release of the air from the vest can be automated employing the ECM unit 205. Therefore, the computer system 206 also comprises the interface 210 to control the ECM unit 205. The system may be adapted in such a manner that in a first step any available pressure from the vest is released and an automated ECG measurement is performed. After finishing the ECG measurement, in a second step air pressure is provided to the connector of the vest to switch the switches to the MR safe, i.e. open state. Then, automatically an MRI measurement is performed. The results from ECG and MRI are then analyzed. In another embodiment, the interface 210 is used to enable the ECM unit 205 to inhibit any MR scanning or to allow only MR scanning with very low RF transmission power.

It has to be noted, that any suitable medium may be used to operate the switches. This includes air, nitrogen or helium, but also any non-conductive or highly resistive liquid which does not disturb the MR image to be acquired.

FIGS. 4A and 4B depict an alternative embodiment of a switch 202, wherein FIG. 4A shows the closed state of the switch and FIG. 4B shows the open state of the switch. The switch 202 comprises conducting elements 408, wherein the elements 408 are fixed to a removable layer 406. The switching from the closed to the open state is performed by moving or even removing the layer 406 thus interrupting the contacts between the wires 102. In the open state, a gap 404 is present between the wires 102. The switching between the closed and the open state is performed by a movement of the strip, i.e. the layer 406 in direction 400.

Thus, in this embodiment several removable strips are used to segment the long wires. Each strip is placed across non-conductive gaps arranged in the long wires. Each strip contains multiple conductive bridges that close the respective gaps. If the strip is removed, the open gaps in the long wires of the vest remain, effectively segmenting these wires into short sections. Patent fasteners 402 may be used to reproduce a positioning and fixation of the layer and thus the conducting elements to the vest.

In addition or alternatively, it is also possible to provide highly resistive wires 102 with a resistivity of at least 2 kOhm/m. Preferably, the wires 102 have a resistivity of 5 kOhm/m. This permits to dampen an RF resonances and avoid MR image artifacts but still allows transmission of the ECG signals.

The invention claimed is:

1. An electrocardiograph sensor, comprising:
   an electrocardiograph sensor mat;
   a plurality of electrodes attached to the mat for acquiring cardiac signals from an object to be examined when the mat is arranged in contact with the object; and
   a plug connected to the electrodes by electric wires, the electric wires being segmented by switches, respectively, each of the switches having a connector and being operable by pressurized gas supplied through the connector,
   wherein the pressurized gas is selectively supplied to each of the switches by an interface to switch between closed and open states.

2. The electrocardiograph sensor of claim 1, wherein the switches are configured for being switched from the open state to the closed state upon reception of the pressurized gas.

3. The electrocardiograph sensor of claim 2, wherein the switches are configured for automatically switching from the closed state to the open state upon release of the pressurized gas.

4. The electrocardiograph sensor of claim 1, wherein the segmentation of the electric wires by the switches results in electrical wire segments, wherein a length of each of the electrical wire segments is equal to or less than an optimal length.

5. The electrocardiograph sensor of claim 4, wherein the optimal length is given by a length at which a magnetic resonance scan of the object in contact with the mat results in:
   a magnetic resonance image with artifacts due to the presence of the electrical wire segments being below a predefined threshold, and/or a local heating of the electrodes and the electrical wire segments due to magnetic resonance scan induced Eddy-currents being below a predefined threshold.

6. The electrocardiograph sensor of claim 1, wherein the mat is comprised in a garment, the garment being wearable by an associated patient for performing the acquisition of the cardiac signals.

7. The electrocardiograph sensor of claim 1, wherein the plug is attached to the mat.

8. The electrocardiograph sensor of claim 1, wherein at least one of the switches segments an electric wire located between two electrodes of the plurality of electrodes.

9. The electrocardiograph sensor of claim 1, wherein at least one of the switches segments an electric wire located between an electrode of the plurality of electrodes and the plug.

10. The electrocardiograph sensor of claim 9, wherein all of the switches segment electric wires located between the plurality of electrodes and the plug, respectively.

11. The electrocardiograph sensor of claim 1, wherein each of the switches comprises:
a chamber configured to receive the pressurized gas; and
an interrupt contact movable between the open state and the closed state in response to pressure resulting from presence of the pressurized gas in the chamber, wherein the interrupt contact provides an electrical interconnection in the closed state.

12. The electrocardiograph sensor of claim 11, wherein each of the switches further comprises:
a spring exerting pressure in an opposite direction from the pressure resulting from the presence of the pressurized gas.

13. The electrocardiograph sensor of claim 12, wherein the interrupt contact is in the open state when the pressure exerted by the spring is greater than the pressure from the presence of the pressurized gas in the chamber, and wherein the interrupt contact is in the closed stated when the pressure from the presence of the pressurized gas in the chamber is greater than the pressure exerted by the spring.

14. The electrocardiograph sensor of claim 11, wherein the interrupt contact is in the closed state when the pressurized gas substantially fills the chamber.

15. An electrocardiograph sensor, comprising:
an electrocardiograph sensor mat;
a plurality of electrodes coupled to the mat for acquiring cardiac signals from an object to be examined;
a plug coupled to the mat, the plug configured to be coupled to an electro-cardiographic mapping (ECM) unit;
a plurality of segmented electric wires coupled to the mat, each of the segmented electric wires being arranged between two electrodes of the plurality of electrodes or between an electrode of the plurality of electrodes and the plug; and
a plurality of switches corresponding to the plurality of segmented electric wires for selectively connecting the two electrodes or the electrode and the plug between which each segmented electric wire is arranged, respectively,
wherein each switch is operable using pressurized gas, wherein supplying and releasing the pressurized gas to and from the switch moves an interrupt contact to selectively close and open an electrical connection across the corresponding segmented electric wire.

16. The electrocardiograph sensor of claim 15, further comprising:
tubes contained in the electrocardiograph sensor mat connected to the plurality of switches and to a central connector to which a pressure actuator is attached.

17. The electrocardiograph sensor of claim 16, wherein the pressure actuator comprises a syringe.

18. The electrocardiograph sensor of claim 16, wherein when the pressure actuator pumps the pressurized gas through the connector, the interrupt contacts of the plurality of switches close the electrical connections across the corresponding segmented electric wires, for ECM operation.

19. The electrocardiograph sensor of claim 18, wherein when the pressure actuator releases the pressurized gas, the interrupt contacts of the plurality of switches open the electrical connections across the corresponding segmented electric wires, for magnetic resonance (MR) scanning operation.

20. An electrocardiograph sensor, comprising:
an electrocardiograph sensor mat;
an electrode on or in the mat for acquiring cardiac signals from an object to be examined when the mat is arranged in contact with the object;
a segmented electric wire on or in the mat, and arranged between the electrode and a plug, the plug being configured to output signals from the electrode;
a switch connected to the segmented electric wire for selectively connecting the electrode and the plug, wherein the switch is operable using pressurized gas; and
at least one tube on or in the mat, the at least one tube being configured to supply the pressurized gas to the switch responsive to a pressure actuator,
wherein the switch comprises:
a chamber configured to receive the pressurized gas via the at least one tube; and
an interrupt contact movable from an open state to a closed state in response to pressure resulting from presence of the pressurized gas in the chamber, wherein the interrupt contact provides an electrical interconnection in the segmented electric wire in the closed state.

* * * * *